(12) United States Patent
Fonte et al.

(10) Patent No.: US 9,862,740 B2
(45) Date of Patent: Jan. 9, 2018

(54) PROCESS FOR PREPARING NOVEL FORMS OF TIACUMICIN B

(71) Applicant: Olon S.P.A., Rodano (MI) (IT)

(72) Inventors: Piera Fonte, Turin (IT); Giovanni Lazzari, Settimo Torinese (IT)

(73) Assignee: OLON S.P.A., Rodano (IT)

( * ) Notice: Subject to any disclaimer, the term of this patent is extended or adjusted under 35 U.S.C. 154(b) by 33 days.

(21) Appl. No.: 15/118,862

(22) PCT Filed: Feb. 25, 2014

(86) PCT No.: PCT/EP2014/053620
§ 371 (c)(1),
(2) Date: Aug. 13, 2016

(87) PCT Pub. No.: WO2015/127956
PCT Pub. Date: Sep. 3, 2015

(65) Prior Publication Data
US 2017/0057988 A1    Mar. 2, 2017

(51) Int. Cl.
*C07H 17/08* (2006.01)
*C07H 1/08* (2006.01)

(52) U.S. Cl.
CPC ............. *C07H 17/08* (2013.01); *C07H 1/08* (2013.01); *C07B 2200/13* (2013.01)

(58) Field of Classification Search
None
See application file for complete search history.

(56) References Cited

U.S. PATENT DOCUMENTS

| 3,978,211 A | 8/1976 | Coronelli et al. |
| 7,378,508 B2 | 5/2008 | Chiu et al. |
| 2013/0303472 A1 | 11/2013 | Fonagy et al. |

FOREIGN PATENT DOCUMENTS

CN    103275153 A    9/2013

OTHER PUBLICATIONS

Search Report and Written Opinion of PCT/EP2014/053620 dated Apr. 17, 2014.

*Primary Examiner* — Layla D Berry
(74) *Attorney, Agent, or Firm* — Silvia Salvadori, P.C.; Silvia Salvadori

(57) ABSTRACT

The present invention relates to a process for obtaining Tiacumicin B with a well defined crystal habit and particle size. The process according to the invention comprises repeating cycles of heating and cooling under controlled conditions of temperature and stirring.

11 Claims, 4 Drawing Sheets

| D(0,1) | D(0,5) | D(0,9) |
|--------|--------|--------|
| 3.90   | 11.36  | 27.35  |

(Example 2)

(Example 3)

(Example 2)

(Example 3)

PROCESS FOR PREPARING NOVEL FORMS OF TIACUMICIN B

This application is a U.S. national stage of PCT/EP2014/053620 filed on 25 Feb. 2014, the content of which is incorporated herein by reference in its entirety.

FIELD OF THE INVENTIONS

The present invention relates to a process for obtaining a new crystal of Tiacumicin B with a well defined crystal habit and particle size. The process according to the invention is efficient and provides an API which is suitable for formulation purposes.

BACKGROUND

Tiacumicin B belongs to the family of Tiacumicins; Tiacumicins, produced by fermentation of *Dactylosporangium aurantiacum*, are a group of unsaturated 18-membered macrocyclic of the macrolide class that differs in the type of substituents of the unsaturated ring. Tiacumicin B has the structure shown below:

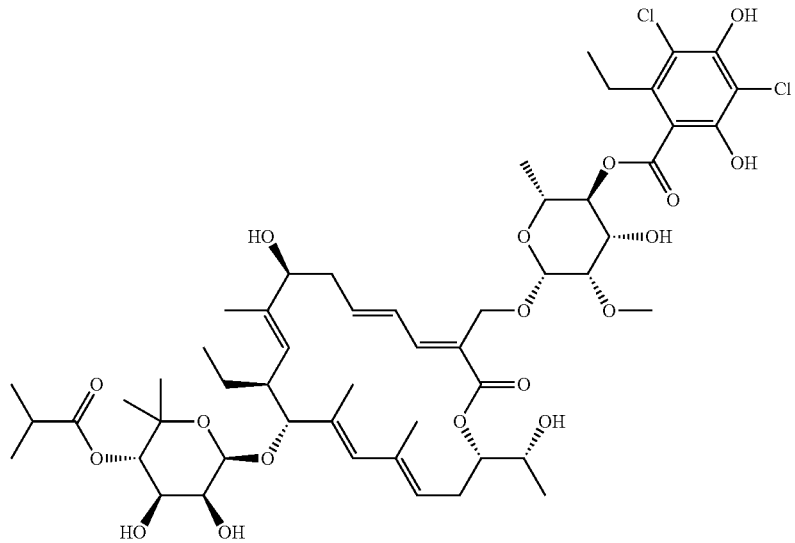 [SMILES: CCc1c(Cl)c(O)c(Cl)c(O)c1C(=O)O[C@H]1[C@H](O)[C@H](OC)[C@H](OC/C2=C\C=C\C[C@H](O)/C(C)=C/[C@H](CC)[C@@H](O[C@@H]3OC(C)(C)[C@@H](OC(=O)C(C)C)[C@H](O)[C@@H]3O)/C(C)=C/C(C)=C/C[C@@H]([C@@H](C)O)OC2=O)O[C@@H]1C]

Tiacumicins and in particular Tiacumicin B show activity against a variety of bacterial pathogens including *Clostridium difficile*.

The API crystallization process and crystal properties have a significant effect on downstream processing and formulation. Physical properties such as particle size, crystal habit, and surface properties are important aspects of API product quality and must be considered with great care and attention during the development of an API crystallization process.

For example, for insoluble or dissolution-limited drug substances, small particle size is necessary to maximize surface area to enhance bioavailability.

For development of drug product processes, particle uniformity may be critical to the homogeneity of a blend or granulation, which directly correlates with the content uniformity and dissolution properties of the drug product. In addition, API crystal properties, such as particle size distribution, habit, and surface properties, have a large effect on bulk powder properties, which may affect formulation operations such as blending, granulation, and compaction. Therefore, having consistent and optimal physical properties of the API is essential for development of formulation processes to produce consistent and reliable drug products.

There are several patents claiming different crystal forms of Tiacumicin B (U.S. Pat. No. 7,378,508, US 2013/0303472). The different polymorphic forms have the drawback to be fragile yielding a final API with a high amount of fine particles that makes the product difficult to formulate.

The control objectives for batch crystallization processes can be defined in terms of product purity, crystal habit, morphology, average particle size, crystal size distribution, bulk density, product filterability, and dry solid flow properties. It is known that the size, shape, and solid-state phase of the product crystals are dependent from the crystallization process.

The procedures described in the prior art suffer both for some drawbacks; U.S. Pat. No. 3,978,211 discloses a crystallization procedure yielding a well defined polymorph but an acicular shape and fragile crystals. In addition, the crystals obtained have a high amount of fine that make the product difficult to formulate. U.S. Pat. No. 7,378,508 discloses a procedure which requires about 3 to about 14 days, therefore not suitable for industrial application. In patent application US 2013/0303472, more suitable procedures are described, which on the other hand require high stressed drying conditions.

There is still a need to find a new crystal habit with improved hardness that can be easily formulated. Here will be disclosed a new crystal habit for Tiacumicin B and a new process for obtaining it.

SUMMARY

The present invention provides an improved crystallization process for Tiacumicin B that results in a crystal having a defined habit a particle size distribution. The new process provides relatively larger, better defined crystals along with narrow particle size distribution and few fines.

DETAILED DESCRIPTION OF THE INVENTION

Figure 1:
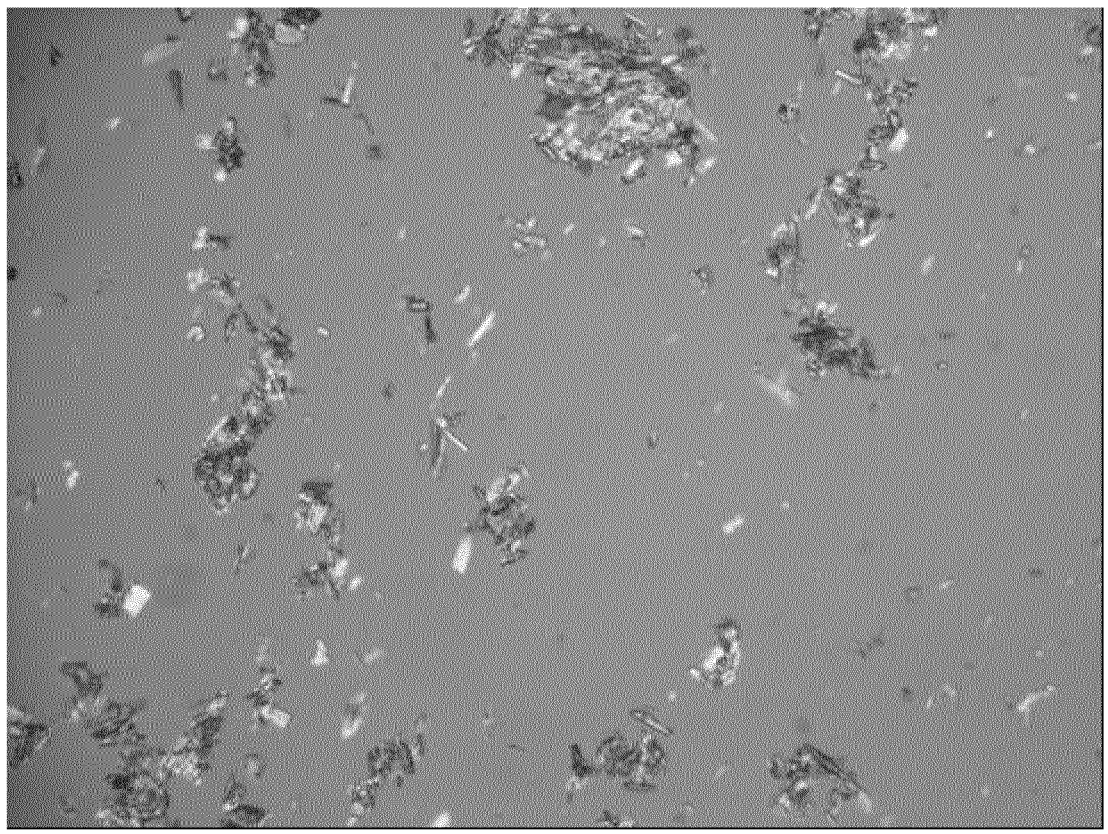
FIG. 1: Shows the Optic Microscopic image of particles obtained with the standard process

The present invention relates to a process for crystallization of Tiacumicin B comprising steps of:
 a) dissolving Tiacumicin B in a solvent;
 b) heating the solution up to a temperature from 30° C. to 50° C. under stirring at a stirring speed from 20 rpm to 400 rpm;
 c) adding an antisolvent in a period of time from 30 minutes to 90 minutes;
 d) reducing the stirring speed to 0 rpm-200 rpm;
 e) cooling the suspension at a temperature from 2° C. to 8° C. in a period of time from 30 min. to 2 h.;
 f) repeating cycles of heating and cooling wherein the heating temperature is lower than the heating temperature of the previous cycle; the cooling temperature is from 2° C. to 8° C. and the cooling time is 30 min. to 2 h.

Surprisingly we have found that by a process of several cycles of heating and cooling it is possible to obtain a well defined rod like crystal shape. In fact while it is known that by repeated cycles of heating and cooling it is possible to increase the particle size distribution of organic compounds it was not predictable that this can also effects the crystals shape.

A distinct advantage of the present invention is that this new crystal shape has relatively high hardness properties and it is not fragile. Therefore as a consequence it is also possible to obtain a well defined particle size as desired by controlling the speed rate of the agitation during crystallization. Alternatively the particle size can be modulated by milling or micronization avoiding crystal fractures that lead to uncontrolled and random results.

For example crystal size in batch crystallizer decrease with increase in stirrer speed; however for each phase of crystallization there is an optimum for agitation speed that allows to crystals remain in suspension for a longer time and provide a larger surface area to grow.

Tiacumicin B used in the process of the present invention is purified Tiacumicin B obtainable by methods known in the art (U.S. Pat. No. 3,978,211; MI2012A001406; MI2012A000560).

The solvent of step a) preferably is selected from the group consisting of methanol, ethanol, isopropanol, diethylether or a mixture thereof, most preferably the solvent is a mixture of methanol and ethyl ether in a ratio from 2:1 to 1:2.

The antisolvent of step c) is preferably a $C_4$-$C_8$ alkane or cycloalkane or a mixture thereof. Most preferably the antisolvent is selected from the group consisting of n-pentane, n-hexane, n-pentane, cyclohexane and light-petroleum or a mixture thereof.

Preferably the ratio between the solvent of step a) and the antisolvent of step c) is from 1 to 3.

The heating temperature of each cycle of step f) is preferably at least 5° C. lower than the heating temperature of the previous cycle and the cycles of heating and cooling of step f) are at least 2.

A further object of the present invention are crystals of Tiacumicin B having rod like crystal shape and a particle size distribution with D90>30 obtained by the above described process.

An other object of the present invention is a pharmaceutical composition comprising the crystals of Tiacumicin B obtained by the above described process in association with a pharmaceutically acceptable carrier.

Example 1 (Comparative Example from U.S. Pat. No. 3,978,211)

Figure 2:
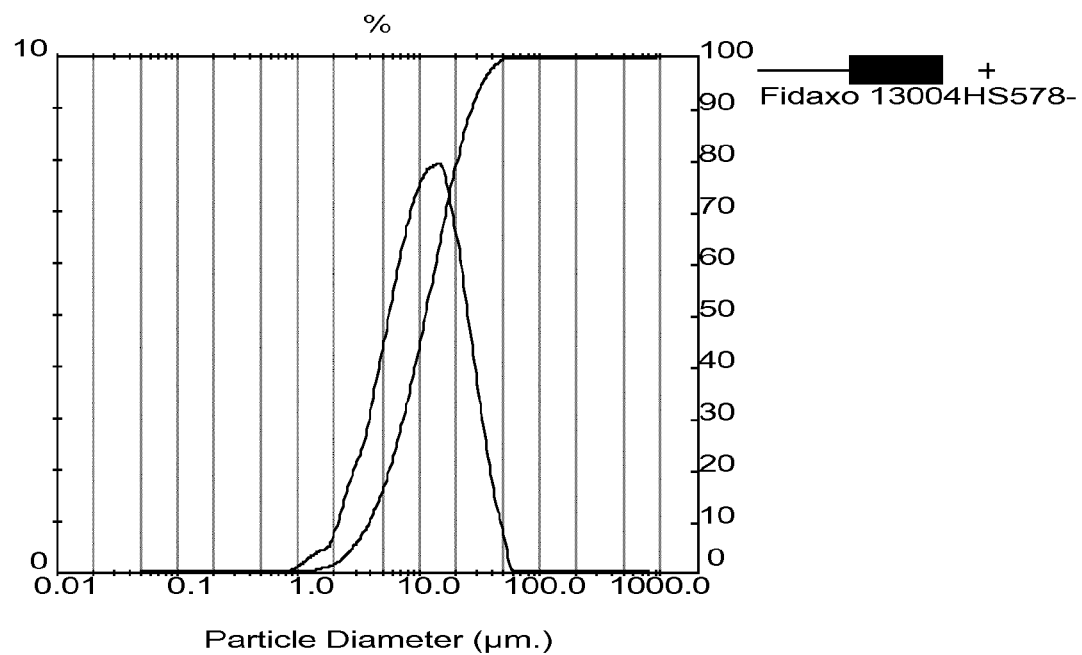
FIG. 2: Shows the Particle size distribution of particles obtained with the standard process

3000 g of pure Tiacumicin B were dissolved in about 40 L of $CH_3OH$. 80 L of $(C_2H_5)_2O$ were added under stirring to the solution at the room temperature. The solution was then heated at 39° C. and the mixer speed was set at 20 rpm; 160 L of n-Pentane were added in about 30 minutes. The mixer speed was then set at 15 rpm and the solution was cooled at 5° C. in about 5 hours. The suspension was then filtered and product dried under vacuum. The crystal obtained has a not well defined crystal shape and a high amount of fine that make the product difficult to formulate. See FIGS. 1 and 2 and Table.

TABLE

| | Psd comparison | | |
|---|---|---|---|
| | D(0.1) | D(0.5) | D(0.9) |
| Example 1 | 3.90 | 11.36 | 27.35 |
| Example 2 | 10.82 | 35.94 | 73.79 |
| Example 3 | 7.04 | 23.98 | 55.27 |

Example 2

Figure 3:
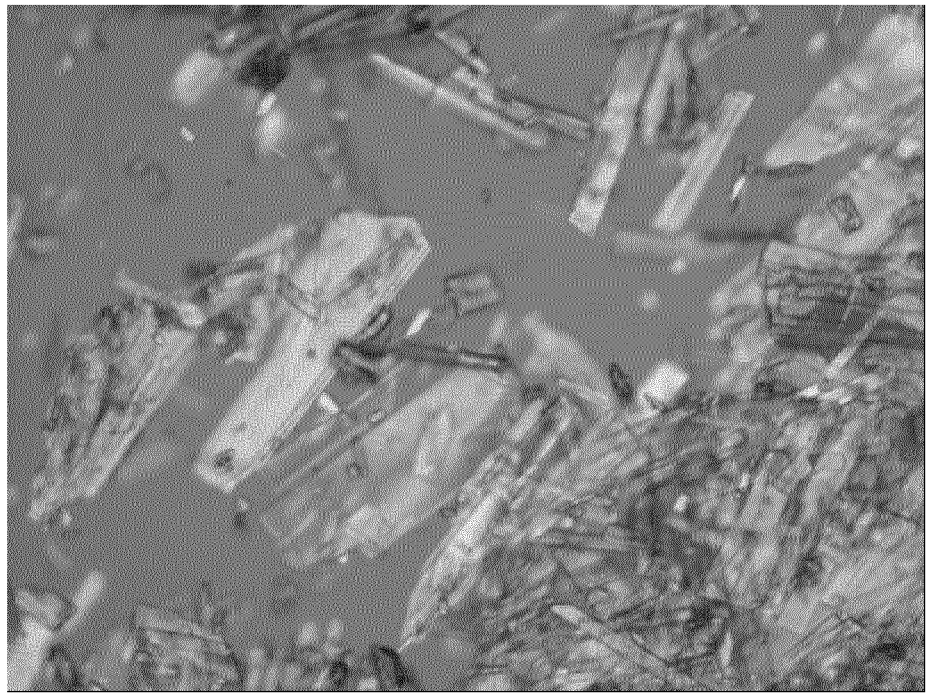
FIG. 3: Shows the Optic Microscopic images of particles obtained with the new improved process (example 2 and 3)
Figure 3:
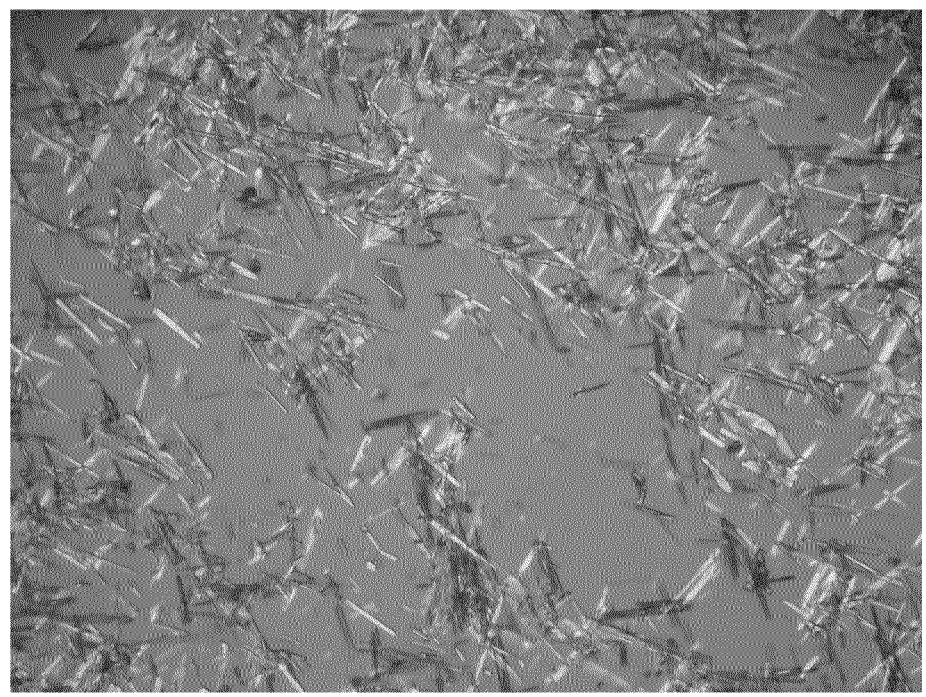
Figure 4:
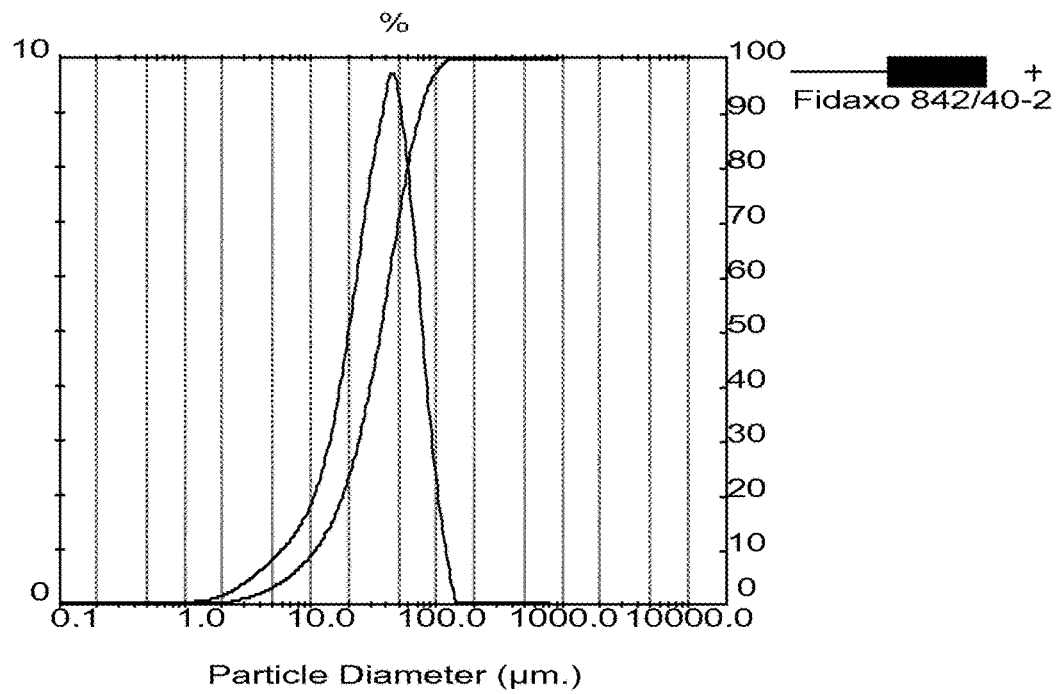
FIG. 4: Shows the Particle size distribution of particles obtained with the new improved process (example 2 and 3)
Figure 4:
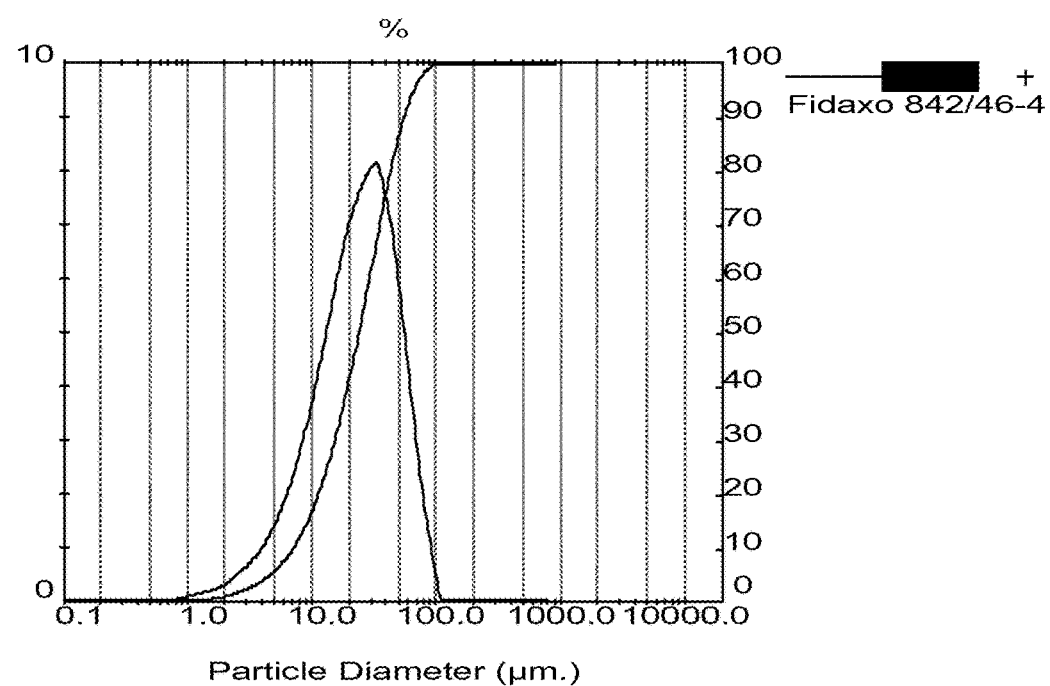

2,5 of pure Tiacumicin B were dissolved in 33 mL of $CH_3OH$. 66 mL of $(C_2H_5)_2O$ were added under stirring to the solution at the room temperature. The solution was then heated at 39° C. and the mixer speed was set at 400 rpm; 132 mL of n-Pentane were added in about 30 minutes. The mixer speed was then set at 200 rpm and the solution was cooled at 5° C. in about 60 minutes. The suspension was heated at 30° C. and maintained at this temperature for about 30 minutes; then the suspension was cooled at 5° C. in about 60 minutes. The suspension was heated at 25° C. and maintained at this temperature for about 30 minutes; then the suspension was cooled at 5° C. in about 60 minutes. The suspension was heated at 15° C. and maintained at this temperature for about 30 minutes; then the suspension was cooled at 5° C. in about 60 minutes and maintained in this condition over night. The crystals obtained has a different more homogeneous and regular crystal habit respect to that obtained with the standard process and an improved psd (see FIGS. 3 and 4 and Table).

Example 3

2000 g of pure Tiacumicin B were dissolved in 26 L of $CH_3OH$. 52 L of $(C_2H_5)_2O$ were added under stirring to the solution at the room temperature. The solution was then heated at 39° C. and the mixer speed was set at 20 rpm; 130 L of n-Pentane were added in about 30 minutes. The mixer speed was then set at 8 rpm and the solution was cooled at 35° C. and maintained at this temperature for about 60 minutes. The suspension was cooled at 30° C. and maintained at this temperature for about 60 minutes. Then the suspension was cooled at 25° C. and maintained at this temperature for about 30 minutes. Then the suspension was cooled at 20° C. and maintained at this temperature for about 30 minutes. Then the suspension was cooled at 15° C. and maintained at this temperature for about 30 minutes. Then the suspension was cooled at 10° C. and maintained at this temperature for about 30 minutes. Then the suspension was cooled at 5° C. and maintained at this temperature for about 30 minutes. The suspension was heated at 30° C. and maintained at this temperature for about 30 minutes; then the suspension was cooled at 5° C. in about 60 minutes. The suspension was heated at 25° C. and maintained at this temperature for about 30 minutes; then the suspension was cooled at 5° C. in about 60 minutes. The suspension was heated at 15° C. and maintained at this temperature for about 30 minutes; then the suspension was cooled at 5° C. in about 60 minutes and maintained in this condition over night. The crystals obtained has a different more homogeneous and regular crystal habit respect to that obtained with the standard process and an improved psd (see FIGS. 3 and 4 and Table).

The invention claimed is:

1. A process for crystallizing Tiacumicin B comprising the steps of:
   a) dissolving Tiacumicin B in a solvent;
   b) heating the solution up to a temperature from 30° C. to 50° C. under stirring at a stirring speed from 20 rpm to 400 rpm;
   c) adding an antisolvent in a period of time from 30 minutes to 90 minutes;
   d) reducing the stirring speed to 0 rpm-200 rpm;
   e) cooling the suspension at a temperature from 2° C. to 8° C. in a period of time from 30 min. to 4 h.;
   f) repeating cycles of heating and cooling wherein the heating temperature is lower than the heating temperature of the previous cycle; the cooling temperature is from 2° C. to 8° C. and the cooling time is 30 min. to 4 h.

2. The process according to claim 1 wherein the solvent of step a) is selected from the group consisting of methanol, ethanol, isopropanol, diethyl-ether or a mixture thereof.

3. The process according to claim 1 wherein the antisolvent of step c) is selected from the group consisting of $C_4$-$C_8$ alkanes or cycloalkanes or a mixture thereof.

4. The process according to claim 1 wherein the solvent of step a) is a mixture of methanol and ethyl ether.

5. The process according to claim 1 wherein the antisolvent of step c) is selected from the group consisting of n-pentane, n-hexane, n-pentane, cyclohexane, and light-petroleum or a mixture thereof.

6. The process according to claim 1 wherein the ratio between the solvent of step a) and the antisolvent of step c) is from 1 to 3.

7. The process according to claim 1 wherein the heating temperature of each cycle of step f) is at least 5° C. lower than the heating temperature of the previous cycle.

8. The process according to claim 1 wherein the cycles of heating and cooling of step f) are at least 2.

9. Crystals of Tiacumicin B having rod like crystal shape and a particle size distribution with D90 >30 obtained by the process of claim 1.

10. Pharmaceutical composition comprising the crystals of claim 9.

11. A pharmaceutical composition comprising the crystals of claim 9 in association with a pharmaceutically acceptable carrier.

* * * * *